US00PP28309P3

(12) United States Plant Patent
Kimlinger

(10) Patent No.: US PP28,309 P3
(45) Date of Patent: Aug. 22, 2017

(54) BLACKBERRY PLANT NAMED 'WILLAMETTE THORNLESS MARION'

(50) Latin Name: ***Rubus* L. Subgenus *Rubus***
Varietal Denomination: Willamette Thornless Marion

(71) Applicant: Leonard Joseph Heidt, Mt. Angel, OR (US)

(72) Inventor: Ernest Kimlinger, Woodburn, OR (US)

(73) Assignee: Leonard Joseph Heidt, Mount Angel, OR (US)

( * ) Notice: Subject to any disclaimer, the term of this patent is extended or adjusted under 35 U.S.C. 154(b) by 599 days.

(21) Appl. No.: 13/573,608

(22) Filed: Sep. 28, 2012

(65) Prior Publication Data

US 2014/0096294 P1 Apr. 3, 2014

(51) Int. Cl.
*A01H 5/08* (2006.01)

(52) U.S. Cl.
USPC ..... Plt./203
CPC ..... *A01H 5/0887* (2013.01)

(58) Field of Classification Search
USPC ..... Plt./203
CPC ..... A01H 5/0887
See application file for complete search history.

*Primary Examiner* — Kent L Bell
(74) *Attorney, Agent, or Firm* — Klarquist Sparkman, LLP

(57) ABSTRACT

The present invention relates to a new and distinct cultivar of blackberry plant named 'Willamette Thornless Marion'. The new cultivar originated as a mutation of 'Marion'. It is nearly identical in all ways to 'Marion' except that it does not have thorns.

10 Drawing Sheets

Figure 1:
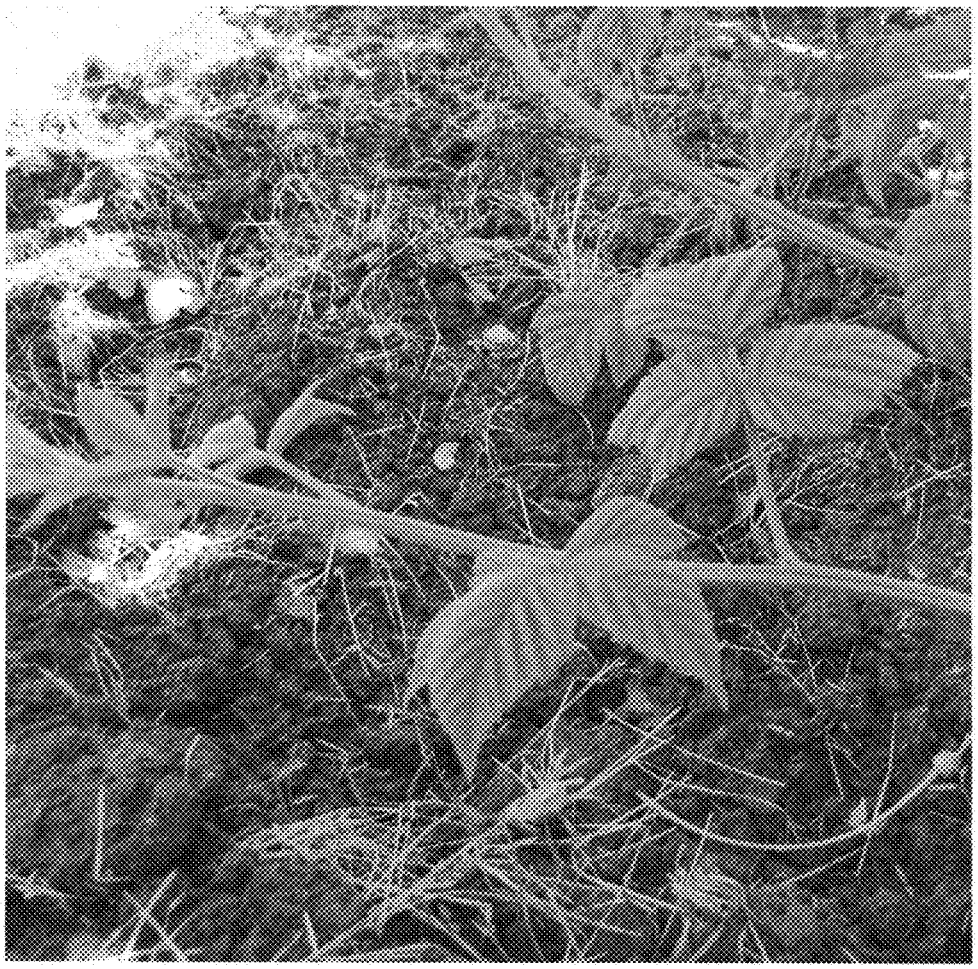

Latin name: *Rubus* L. Subgenus *Rubus*.

Variety denomination: 'Willamette Thornless Marion'.

There was no Federally-Sponsored Research or Development.

BACKGROUND OF THE INVENTION

The new cultivar 'Willamette Thornless Marion' is a thornless (spineless) naturally occurring mutation of the cultivar 'Marion' (non-patented). This new cultivar was discovered as a single primocane cane mutation of a 'Marion' blackberry plant growing in 2005 in a twenty acre field of cultivated 'Marion' plants in Clackamas County, Oreg.

The mutation grew as a single primocane from an established 'Marion' plant. The mutant primocane was observed during the routine hand wrapping of the 'Marion' primocanes on the trellis. New plants were asexually reproduced by tip layering the discovered mutant primocane; micro propagated plants have also been started from the mutant primocane. Both types produce true to type stable plants through successive generations.

The nearest and closest cultivar to the 'Willamette Thornless Marion' is the 'Marion'. We use the 'Marion' for comparison as this new cultivar is a mutation of a 'Marion'. The 'Marion' is a trailing blackberry commercially grown primarily in Oregon. The 'Marion' is widely produced and accounts for more than half of the blackberry production in Oregon. Virtually all blackberries use the 'Marion' (non-patented) as the base of comparison for vigor, color, flavor, production, cold hardiness and all other facets of a blackberry plant either commercially in use or in the development stage.

The main difference between the new cultivar and 'Marion' is that the new cultivar is substantially spineless.

The normal term for spine or spineless, in the blackberry industry, is thorn or thornless). The new cultivar has fine and very few thorns whereas the 'Marion' has hardy thorns throughout the plant. One primary drawback with the 'Marion' is that the stems and petioles, which remain from the first year, have many thorns. The leaflets and leaves do fall off the 'Marion' primocanes during the dormant season; however most stems and petioles remain attached to the primocane. During mechanical harvest, these 'Marion' stems and petioles fall off and attach themselves to the fruit and they then become very difficult to remove. These 'Marion' stems and petioles with thorns then become a problem for producers, processors, and consumers. In contrast, the new cultivar has no spines/thorns on the stems or petioles. In so far as they have been observed, the other aspects of both the new cultivar and the 'Marion' are almost exactly the same with non-significant variations which exist in both cultivars.

COMPARISON TO SIMILAR VARIETIES

The new cultivar (and the 'Marion' cultivar) have vigorously growing trailing vines. During the first year three to five primocanes are produced from 4.5 meters to 7 meters long, depending on the season; in long warm summers the growth can be as much as thirty to forty percent more than in cooler short summers. During the second year these canes then produce floricanes while new primocanes grow from the root of the plant. These floricanes develop from a bud that is protruding from the crook of the previous year's leaf base. From the floricanes, many berries are produced which ripen in mid-summer.

The fruit of both the new cultivar and the 'Marion' are a bright black color whose length is about twice as long as its width. The berry has a tart sweet flavor. Coloring and measurements follow in the botanical description contained below.

The new cultivar, 'Willamette Thornless Marion', originated as a mutation of the 'Marion'. It is nearly identical in all ways except for its thornless characteristics. It has the same color and flavor as the 'Marion', the same growing characteristics, cold hardiness and disease and pest resistance. It harvests at the same time, and processes in a similar manner. The key advantage to this new cultivar is that the problem of stems and petioles with thorns sticking to fruit during mechanical harvest is eliminated by the new cultivar. In addition, since the primocanes do not have thorns, the care and handling of the canes is simplified, and worker fatigue and injury is significantly reduced.

SUMMARY OF THE INVENTION

From the original discovered thornless primocane, several new plants were reproduced in Clackamas County, Oreg. asexually by tip layering, thus giving a true genetic copy of the original. The new cultivar reproduces true to type through successive generations of asexual propagation. Through the sixth generation of asexual propagation, the plants have remained true to type. As with the 'Marion' cultivar, in the first year after planting the primocanes grew vigorously and produced no fruit and reached a length of 4.5 to 7 meters. During the second year these canes then produced fruit while new primocanes grew from the root of the plant.

DESCRIPTIONS OF ILLUSTRATIONS

The accompanying photographs show typical specimens of the fruit, leaves and canes of the new cultivar as well as the typical specimens of the fruit, leaves and canes of the 'Marion'.

FIG. 1: A photograph of the primocane tip of the new cultivar.

Figure 2:
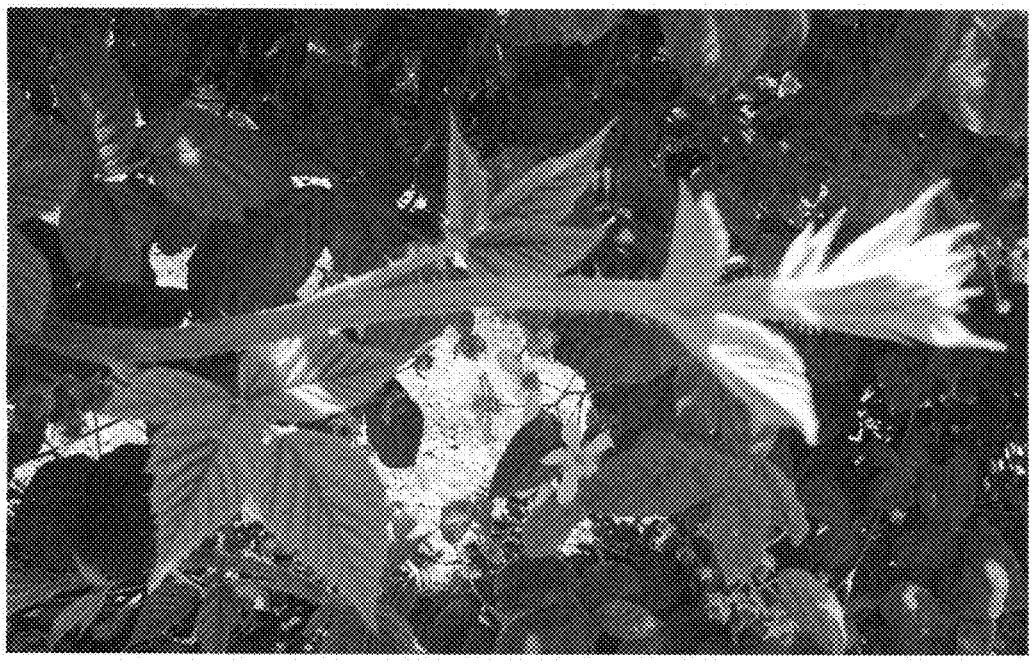

FIG. 2: A photograph of the primocane tip of a 'Marion' blackberry.

Figure 3:
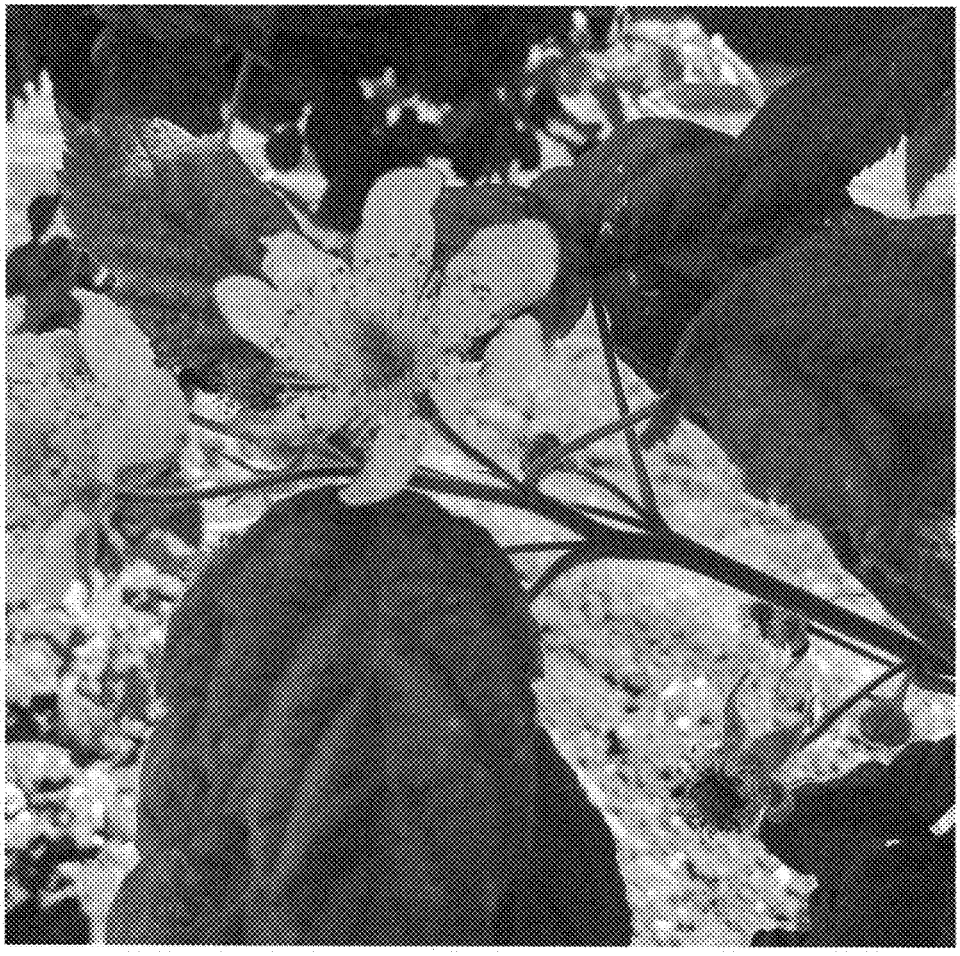

FIG. 3: A photograph of the flower and stems of the new cultivar.

Figure 4:
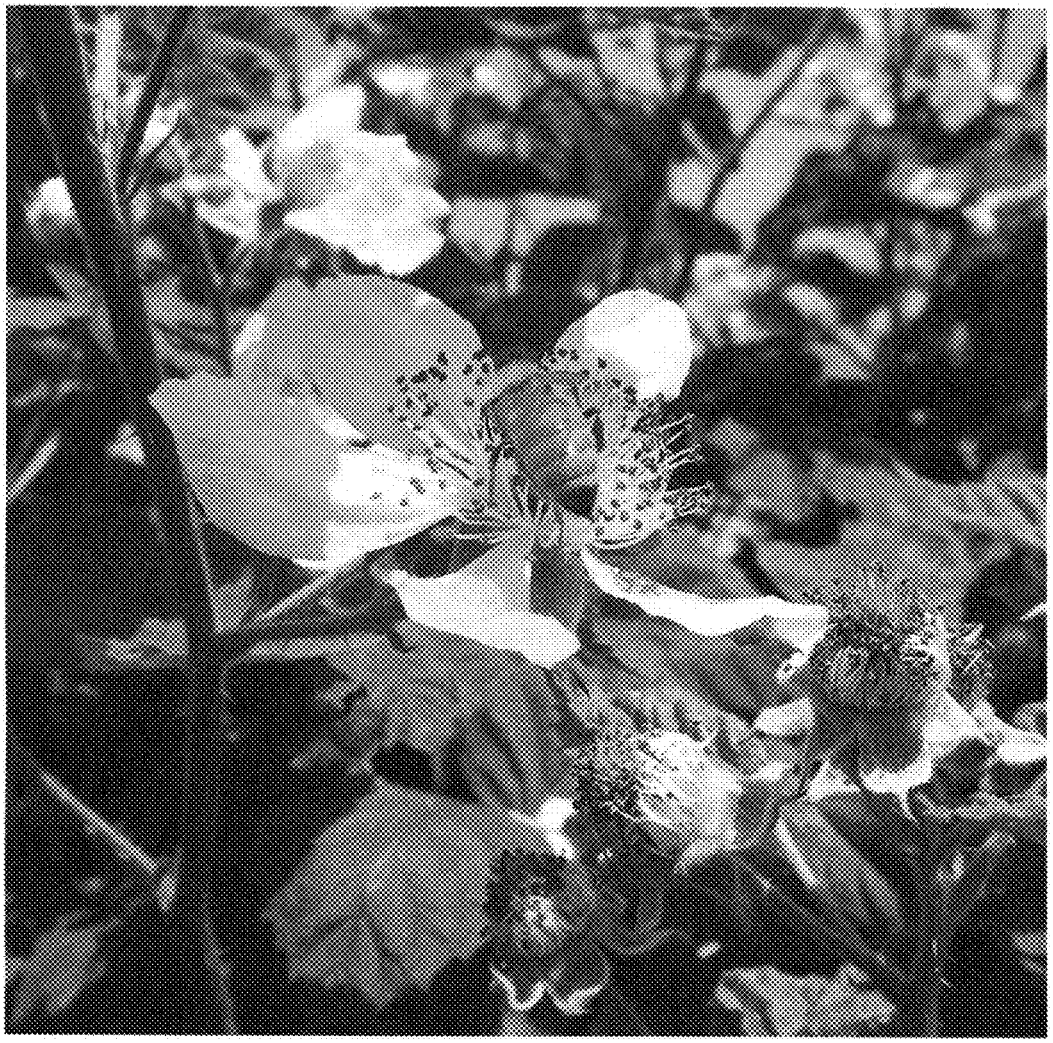

FIG. 4: A photograph of the flower and stems of a 'Marion' blackberry.

Figure 5:
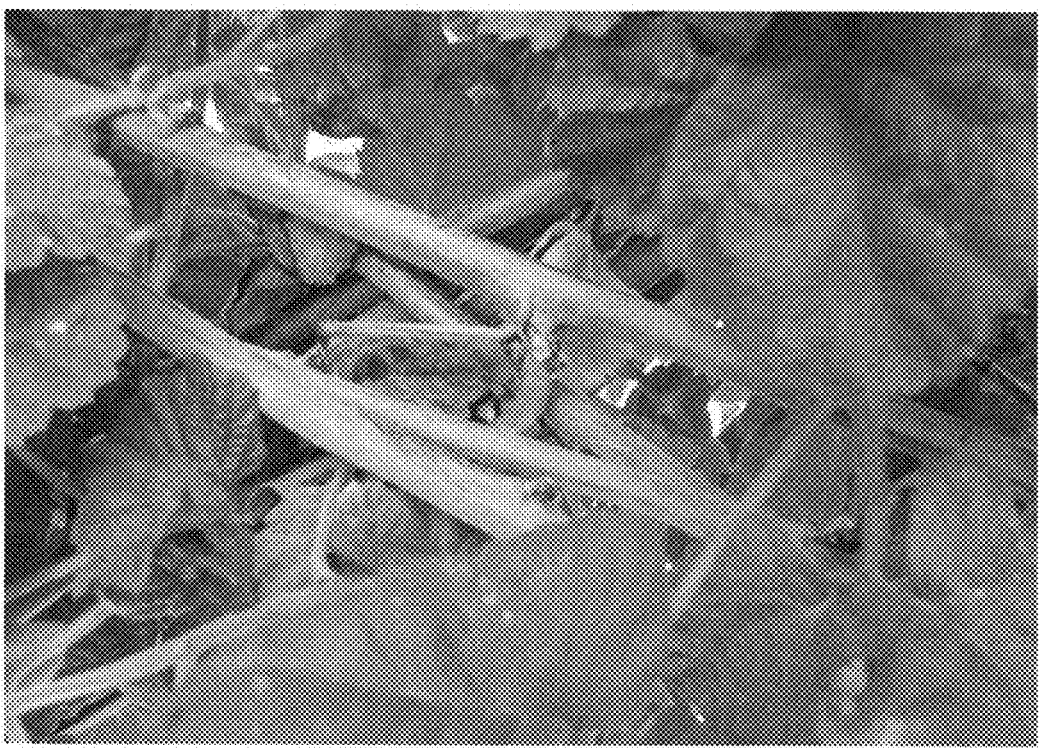

FIG. 5: A photograph of the second year canes of the new cultivar.

Figure 6:
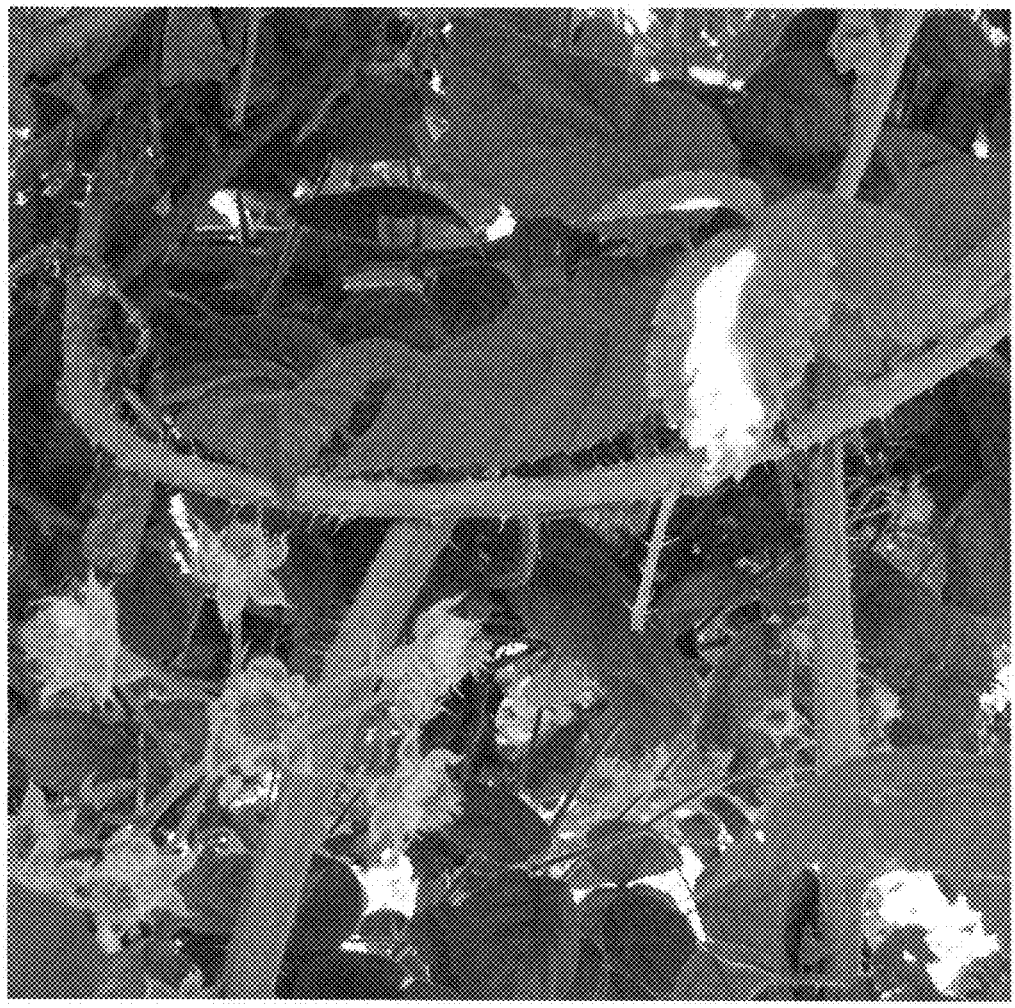

FIG. 6: A photograph of the second year canes of a 'Marion' blackberry.

Figure 7:
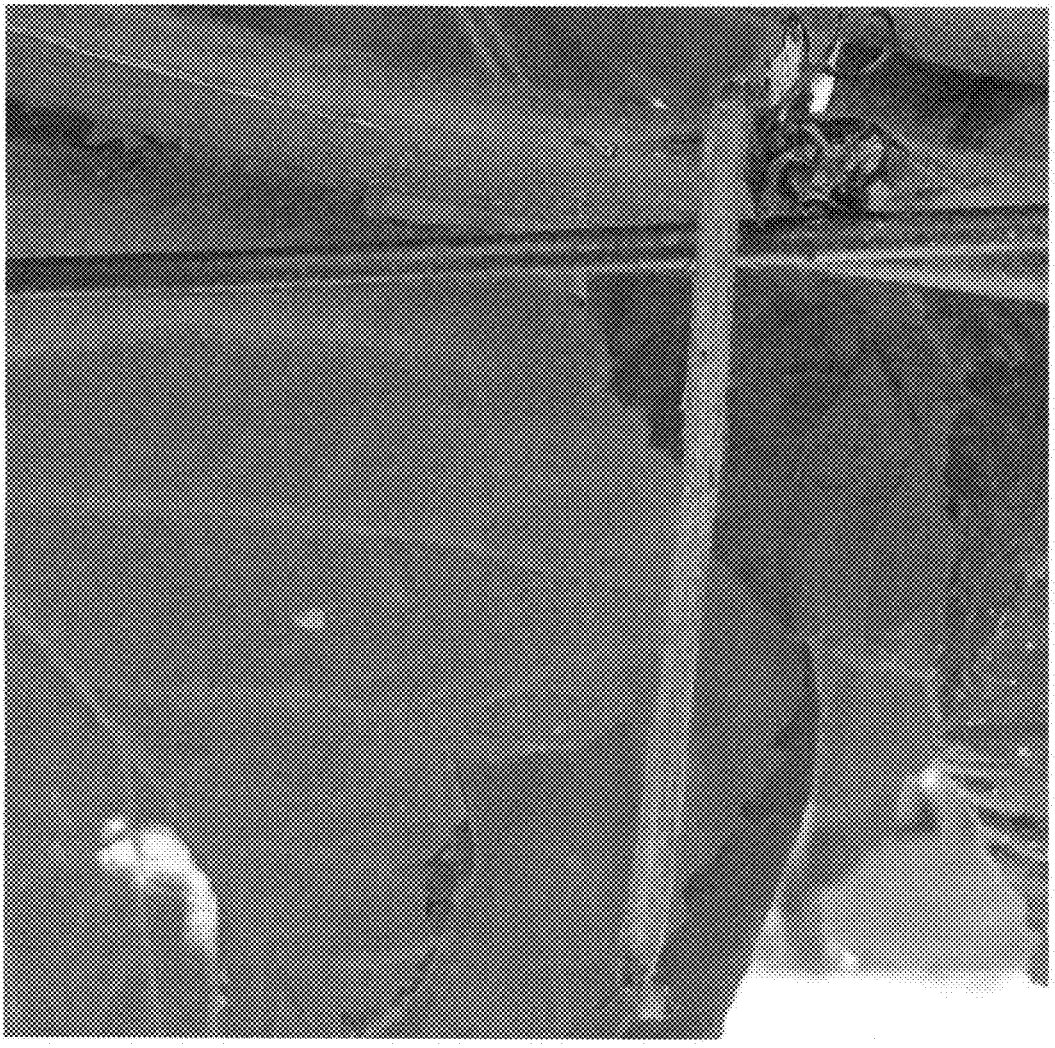

FIG. 7: A photograph of a leaf stem from the new cultivar.

Figure 8:
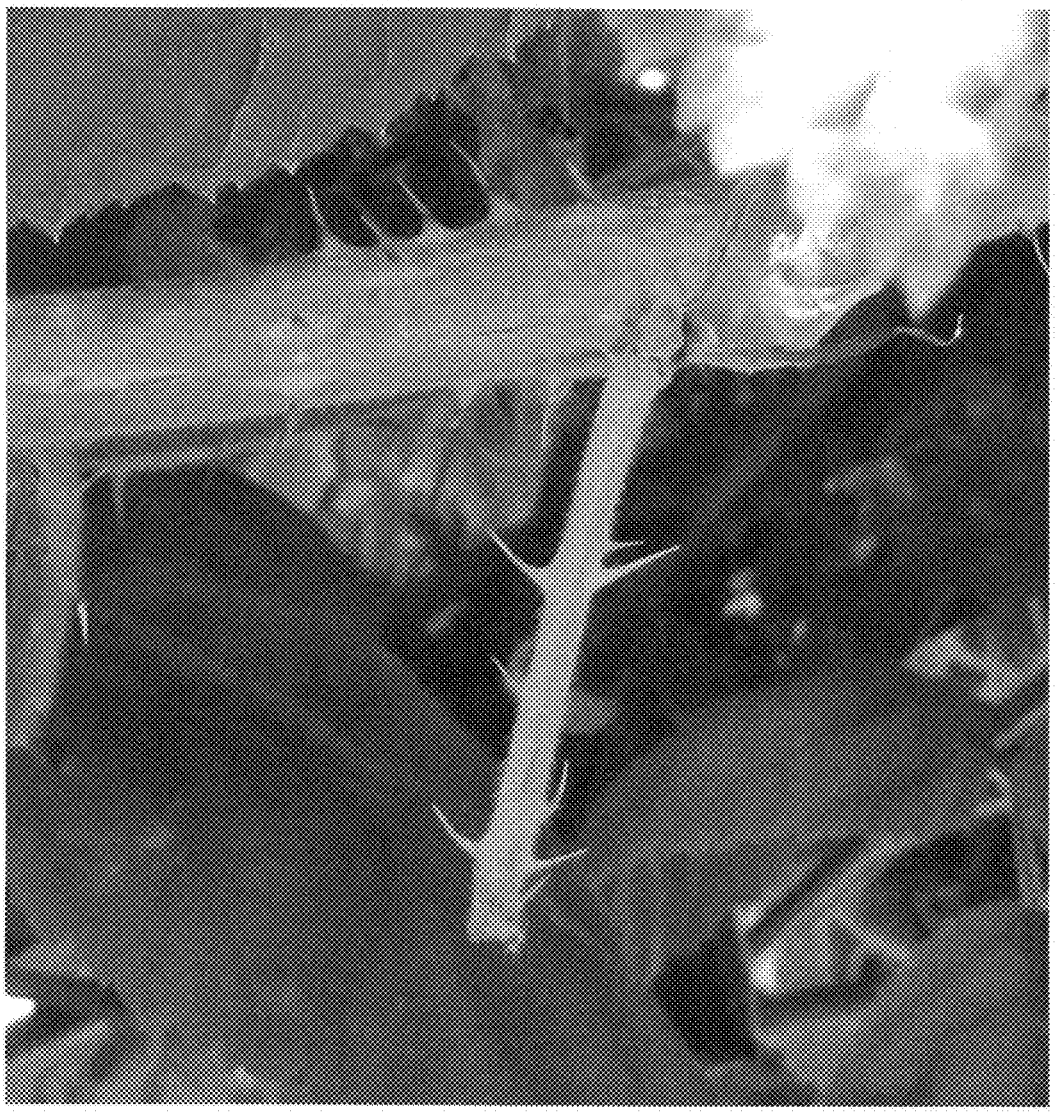

FIG. 8: A photograph of a leaf stem from a 'Marion' blackberry.

Figure 9:
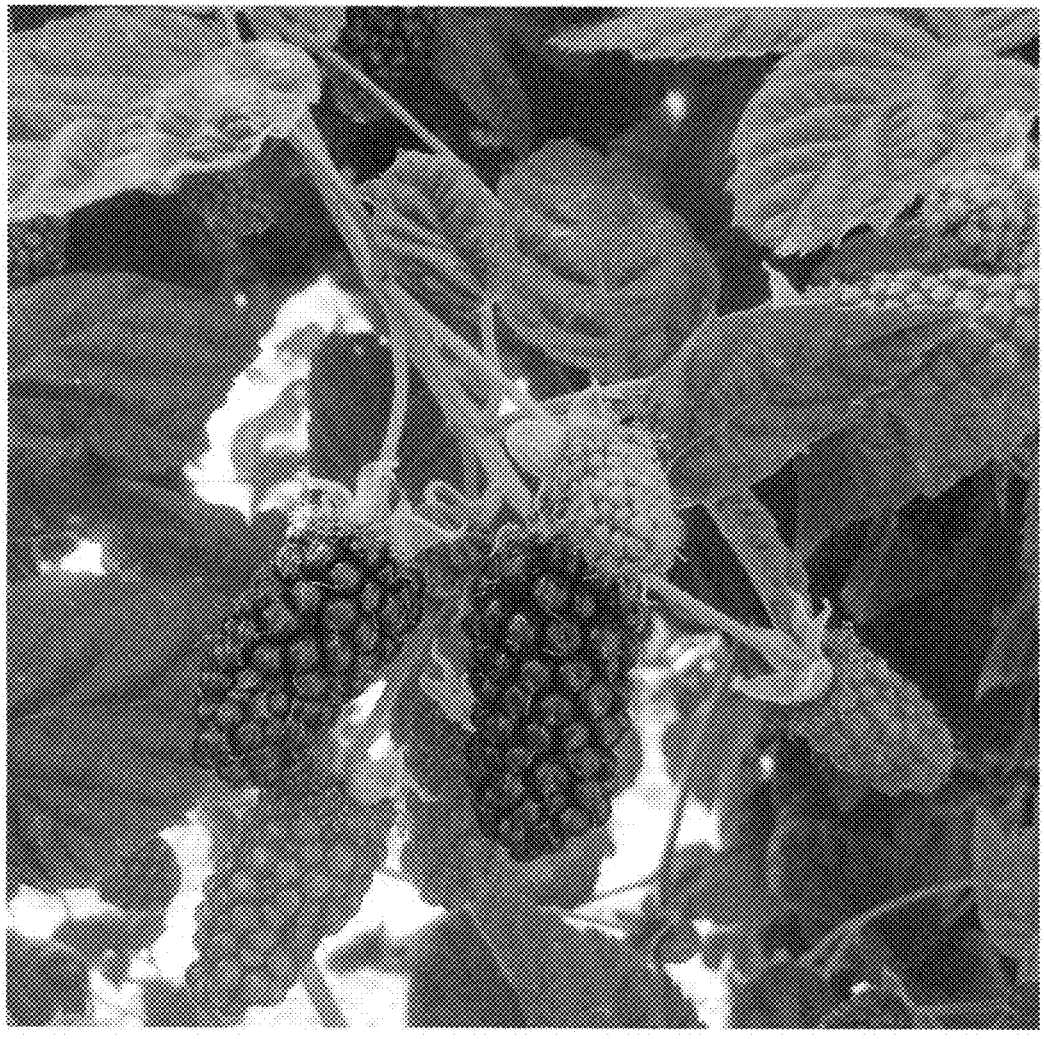

FIG. 9: A photograph of the fruit and stems of the new cultivar.

Figure 10:
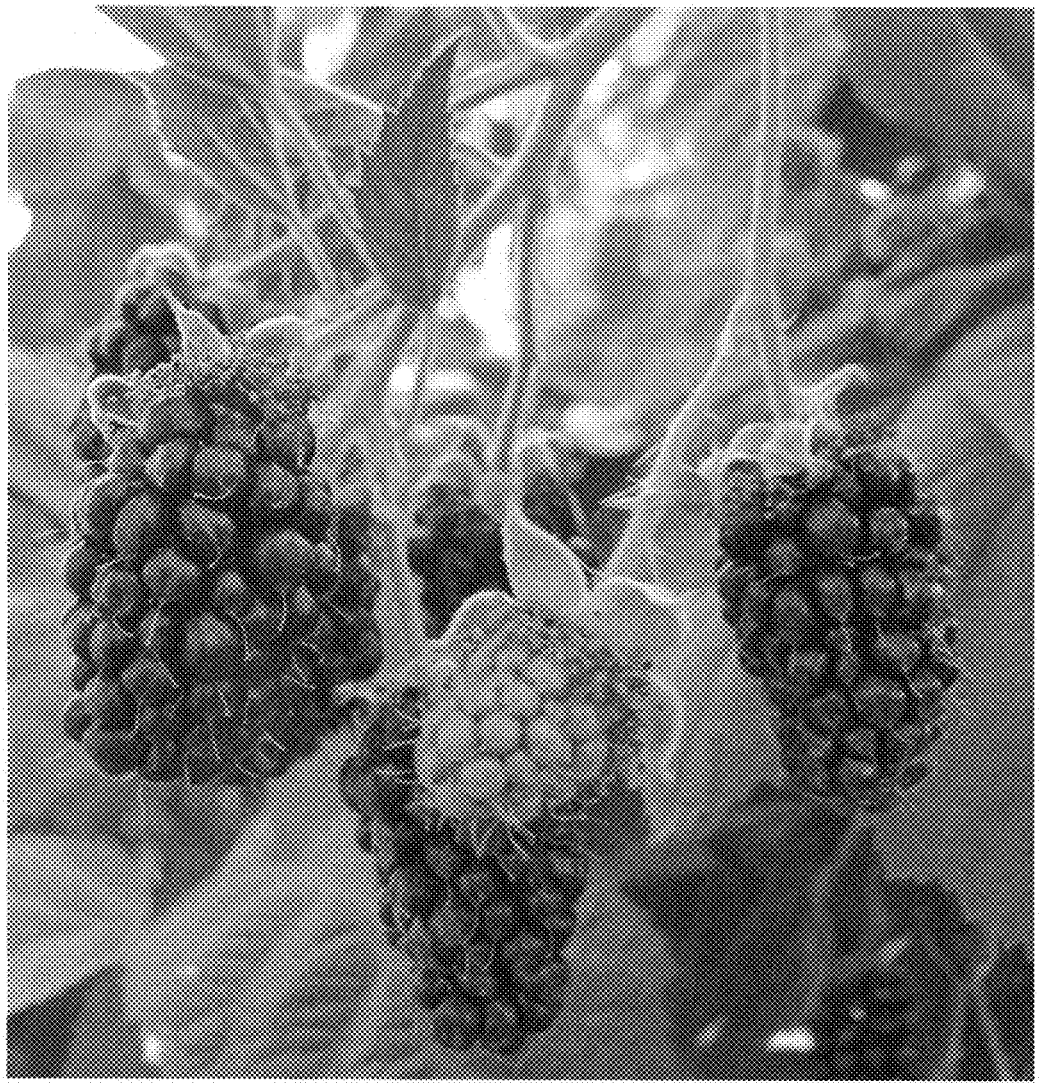

FIG. 10: A photograph of the fruit and stems of a 'Marion' blackberry.

BOTANICAL DESCRIPTION OF THE PLANT

The descriptions are for the plant grown in the Willamette Valley in Oregon from several generations of the same plant. The dimensions, sizes, colors and other characteristics are averages not specifics for a three year old plant. The new cultivar has not been observed under all possible environmental conditions. The Royal Horticultural Colour Chart (R.H.S.) is the comparison chart used in these descriptions.

Plant:

*Canes*.—The plant produces from three to six vigorous primocanes from the root stock each growing season each with a diameter average of 1.2 cm to 1.5 cm. These canes reach the length of 4.5 m to 7 m by the end of the growing season, usually in October in Clackamas County, Oreg. The internode distance varies from 4 cm to 9 cm. During the optimal growing conditions the distance separating internodes gets longer and less during cooler and wet periods. The primocanes begin with short and soft thorns for the first 30 cm to 60 cm then rapidly diminishes and disappears by 90 cm on the remaining growth. There are no thorns on the floricanes. Thorn length is 0.2 cm to 0.3 cm and diameter is 0.04 cm to 0.07 cm. The mean number of thorns is 30 per centimeter within the first 30 cm to 60 cm of the primocane and easily scrape off by a finger or a straight edge. When the primocane has grown past 60 cm virtually no thorns are visible and those that do appear are so fine that they are more like hairs and do not stick into hands or fruit. The 'Marion' has hardy thorns throughout the primocanes and floricanes. These thorns do not break off easily and will stick in the hands if touched and regularly stick to fruit when harvested. Primocane color: Yellow-Green Group (144A); floricanes color: Yellow-Green Group (144B).

*Foliage*.—The leaves are spaced from 4 cm to 9 cm on the primocanes. There are three leaflets per leaf with no variables. The leaf is compound. Each leaflet is ovate and the edges are serrated; serrated teeth length is 0.20 cm and width is 0.35 cm. The mature leaflet apex is broadly acuminate/acute and the leaflet base is round/cordate. Each leaflet varies between 8 cm to 12 cm in length and between 4 cm to 8 cm in width. Both the front and back of each leaflet is velvet in texture. Leaf colors: adaxial — Yellow-Green Group (147B); abaxial — Yellow-Green Group (147B). The petiolule length varies between 0.5 cm and 2.5 cm for each leaflet. The diameter of each petiolule varies from 0.1 cm to 0.2 cm. Petiolule color: Yellow-Green Group (144B). The petiole varies from 3 cm to 5 cm in length and is 0.15 cm to 0.25 cm in diameter. Petiole color: adaxial — Yellow-Green Group (144C); abaxial — Yellow-Green Group (144C). Stipule length is 1.4 cm and width is 0.30 cm. Stipule color: Yellow-Green Group (144C).

*Buds*.—The floricane buds form above each leaf on the primocane grows and are ovate in shape. Initial bud size, once visible, is 0.1 cm long and 0.05 cm in diameter and develops to 0.5 cm long and 0.25 cm in diameter by the time the primocane goes into dormancy. In springtime the bud further develops and begins to grow with flower clusters developing as the floricane reaches 3 cm to 5 cm. The floricane grows to a length of 30 cm to 60 cm with a flower cluster forming periodically along its length. Typically there are 10 to 15 flower buds per floricane. The peduncles range from 2 cm to 14 cm in length and the mean thickness is 0.1 cm and the pedicels range from 2 cm to 7 cm in length and the mean thickness is 0.075 cm. Bud color: Yellow-Green Group (144B); Peduncle color: Yellow-Green Group (144B); Pedicel color: Yellow-Green Group (144B).

*Flowers*.—When the flower bud opens it has a mean diameter of 4.45 cm. There are 5 to 7 petals per flower. The petal is obovate in shape. Length is a mean of 2 cm; width is a mean of 1 cm. Petal color; adaxial color: White Group (155D) abaxial color: White Group (155D) with a pinkish hue when flowers first open; Red Group (49D). The sepals are 5 to 6 per flower bud; they are ovate in shape with an acute apex. The outer color; Yellow-Green Group (144B); inner color; Yellow-Green Group (144C). Once the fruit forms the sepals dry and change colors and curl back away from the fruit Color: Greyed-Orange (165C). The stamens have an erect filament that is white; Yellow-White Group (158C); and the anther is round with the pollen a rusty brown: Greyed-Orange Group (166B); their length is between 0.5 cm and 1 cm. They are numerous with the mean count being 140. The pistils radiate from a conical shape and are numerous as well with a mean count being 80 their length is 0.75 cm their color is a light green; Yellow-Green Group (145C). Pollen is abundant and flowers are self-pollinating. Bloom window is from mid-May through mid-June. Each bloom last for a period of one to two days. Petals fall off as the fruit develops from the center pistils. Typical ovary at peak bloom is conical in shape and light green in color: Yellow-Green Group (144B); diameter is typically 0.5 cm and length is typically 0.8 cm.

*Fruit*.—The fruit matures 6 to 7 weeks after the bloom is finished. The ripe fruit is oblong in shape and comprised of a mean of 80 druplets per fruit whose length is a mean of 4 cm and width is a mean of 2.5 cm. Color: Violet-Blue (N89A) to Black Group (202A). The fine pistil hairs are still evident, but dry, in the ripe fruit. Fruit weight is 3.75 grams and is firm as it begins to ripen then turns soft as it matures in ripeness. Fruit soluble solids is 12.3 (% in Brix), PH is 3.25, titratable acidity is 14.74 (% as citric acid). Yield is 6.30 kg per plant. The fruit taste is the same as the 'Marion' berry which has a tart sweet flavor. It is larger, sweeter and juicier than the most blackberries. The main use of the fruit is in IQF applications (pies, scones, etc.) puree for ice cream and juice products.

*Reproduction*.—The plant is asexually reproduced by tip layering, that is by placing the tip of the primocane in the ground in the fall when the weather turns cool and the plant finishes its growth, then covering it with 2 inches of soil. Then, in the following March, the new plant is clipped free of the primocane and can be replanted when the new shoot is 3 inches or more in length, usually in May. Each primocane tip can be cut off twice during the growing season and ten to twenty new laterals will produce multiple new tips for laying each season. Plants may be reproduced by micro propagation to obtain large volumes in a shorter time period. One thousand micro propagated plants have been grown adjacent to tip layered plants and they remained true to type.

*Cold hardiness*.—The new cultivar demonstrates similar characteristics of the 'Marion' though it has not been observed in all possible environmental conditions. Weather observations over the past 40 years have shown that the 'Marion' sustains slight damage at temperatures of 20 degrees Fahrenheit and medium damage at 10 degrees to 15 degrees Fahrenheit and severe damage below 10 degrees Fahrenheit, depending on the state of dormancy.

*Disease and pest resistance*.—The new cultivar over nine years of observation (2006-2014) has demonstrated the same resistance and susceptibility as the 'Marion' and other 'Marion' type blackberry. The same chemical and fertilizer recommendation for blackberries has been used on this new cultivar and has demonstrated the appropriate response by the new variety to these chemicals and fertilizers.

The invention claimed is:

1. A new and distinct variety of Blackberry plant named 'Willamette Thornless Marion' as illustrated and described herein.

* * * * *

Primocane Tip from a 'Willamette Thornless Marion'

Primocane Tip from a 'Marion'

Flower & Stem from a 'Willamette Thornless Marion'

Flower & Stem from a 'Marion'

Second year canes from a
'Willamette Thornless Marion'

Second year canes from a 'Marion'

Second Year leaf Stem from a
'Willamette Thornless Marion'

Second Year leaf Stem from a 'Marion'

Fruit & Stem from a
'Willamette Thornless Marion'

Fruit & Stem from a 'Marion'